(12) United States Patent
Wang et al.

(10) Patent No.: US 10,695,188 B2
(45) Date of Patent: Jun. 30, 2020

(54) ARTIFICIAL EPISTROPHEUS SUPPORT BODY

(71) Applicant: GUANGZHOU GENERAL HOSPITAL OF GUANGZHOU MILITARY COMMAND, Guangzhou (CN)

(72) Inventors: Jianhua Wang, Guangzhou (CN); Hong Xia, Guangzhou (CN); Qingshui Yin, Guangzhou (CN)

(73) Assignee: GUANGZHOU GENERAL HOSPITAL OF GUANGZHOU MILITARY COMMAND, Guangzhou (CN)

( * ) Notice: Subject to any disclaimer, the term of this patent is extended or adjusted under 35 U.S.C. 154(b) by 23 days.

(21) Appl. No.: 16/088,827

(22) PCT Filed: Aug. 31, 2016

(86) PCT No.: PCT/CN2016/097561
§ 371 (c)(1),
(2) Date: Sep. 27, 2018

(87) PCT Pub. No.: WO2018/000572
PCT Pub. Date: Jan. 4, 2018

(65) Prior Publication Data
US 2019/0105170 A1    Apr. 11, 2019

(30) Foreign Application Priority Data

Jul. 1, 2016    (CN) .......................... 2016 1 0520355

(51) Int. Cl.
*A61B 17/80*    (2006.01)
*A61F 2/44*    (2006.01)
(Continued)

(52) U.S. Cl.
CPC ............ *A61F 2/44* (2013.01); *A61B 17/1757* (2013.01); *A61B 17/7055* (2013.01);
(Continued)

(58) Field of Classification Search
CPC .......... A61F 2/44; A61F 2/244; A61F 2/4446; A61F 2002/30578; A61F 2002/30952;
(Continued)

(56) References Cited

U.S. PATENT DOCUMENTS 6,066,175 A * 5/2000 Henderson ................ A61F 2/44
623/17.11
9,381,093 B1 * 7/2016 Morris ................ A61B 17/7059
(Continued)

FOREIGN PATENT DOCUMENTS

CN        102319129 A        1/2012
CN        102860864      *   1/2013    ................ A61F 2/44
(Continued)

*Primary Examiner* — Pedro Philogene
(74) *Attorney, Agent, or Firm* — Bayramoglu Law Offices LLC

(57) ABSTRACT

The invention discloses an artificial epistropheus support body comprising a support. The support comprises a crown part and a body part, a top surface of the crown part forms a top profiling surface, and a bottom surface of the body part forms a bottom profiling surface; the support has a cavity inside thereof, and a micro-hole grid stent is arranged in the cavity; the cavity forms a plurality of windows on the surface of the support. The bottom end of the body part is provided with a lower fixing lug, while the upper end of the crown part is provided with an upper fixing lug; both the lower fixing lug and the upper fixing lug are provided with fixing holes. The artificial epistropheus support body possesses good stability for supporting and reconstructing, it also can prevent a prosthesis from loosening and failing after surgery.

16 Claims, 5 Drawing Sheets

(51) Int. Cl.
*A61B 17/70* (2006.01)
*A61B 17/17* (2006.01)
*A61F 2/30* (2006.01)

(52) U.S. Cl.
CPC ...... *A61B 17/7059* (2013.01); *A61B 17/8033* (2013.01); *A61B 17/8042* (2013.01); *A61B 17/8061* (2013.01); *A61F 2002/30578* (2013.01); *A61F 2002/30952* (2013.01); *A61F 2002/30985* (2013.01); *A61F 2002/4495* (2013.01)

(58) Field of Classification Search
CPC ... A61F 2002/30985; A61F 2002/4495; A61B 17/1757; A61B 17/7055; A61B 17/7059; A61B 17/8033; A61B 17/8042; A61B 17/8061
USPC .............. 623/17.11–17.16; 606/246–289, 96
See application file for complete search history.

(56) References Cited

U.S. PATENT DOCUMENTS

| | | | |
|---|---|---|---|
| 9,610,174 B2* | 4/2017 | Wang | B22F 3/1121 |
| 10,143,499 B2* | 12/2018 | Milz | A61B 17/7059 |
| 10,390,958 B2* | 8/2019 | Maclennan | A61F 2/442 |
| 2004/0204710 A1* | 10/2004 | Patel | A61B 17/1728 |
| | | | 606/53 |
| 2010/0312345 A1 | 12/2010 | Duffield et al. | |
| 2014/0228960 A1* | 8/2014 | Forterre | A61F 2/447 |
| | | | 623/17.16 |

FOREIGN PATENT DOCUMENTS

| | | | | |
|---|---|---|---|---|
| CN | 102860864 A | | 1/2013 | |
| CN | 202776644 U | | 3/2013 | |
| CN | 203749650 U | | 8/2014 | |
| CN | 203988502 U | | 12/2014 | |
| CN | 204655198 | * | 9/2015 | ............... A61F 2/44 |
| CN | 204655198 U | | 9/2015 | |

* cited by examiner

ARTIFICIAL EPISTROPHEUS SUPPORT BODY

CROSS REFERENCE TO RELATED APPLICATIONS

This application is the national phase entry of International Application PCT/CN2016/097561, filed on Aug. 31, 2016, which is based upon and claims priority to Chinese Patent Application No. 201610520355.2, filed on Jul. 1, 2016, the entire contents of which are incorporated herein by reference.

TECHNICAL FIELD

The invention relates to a technical field of medical apparatus and instruments, and more specifically to an artificial epistropheus support body.

BACKGROUND

Nodules and tumors involving the upper cervical spine usually severely damage the vital structures of the atlantoaxial spine and compress the spinal cord, causing severe consequences of paralysis. It is necessary to perform a surgical resection for such patients, and complete the reconstruction and fixation of damaged structures so as to maintain the integrity and stability of the structure of the craniocervical junction region and preserve normal physiological functions.

The atlantoaxial spine is located at the craniocervical junction region, with a special anatomical structure and a deep position, where important nerve center and blood vessels exist nearby, hence it is difficult to perform a resection and reconstructive surgery in a spine surgery. Such difficulties mainly include: (a) The surgical exposure is more difficult; if the atlantoaxial lesion is to be removed, the transoral approach will be necessary, but if the lesion is larger, or the range of the reconstruction and fixation is relatively wide, you may need to implement an invasive surgical approach, such as a lower jawbone sacrotomy with larger wounds; however, this surgical exposure often requires the cooperation of a dentist. (b) The risk of the surgical operation is high; as we know, the spinal canal of the atlantoaxial spine contains the cervical spinal cord and the medulla oblongata at high level, so the excision of lesions requires superb surgical techniques, any slight carelessness would cause damage to the medulla oblongata, leading to a risk of paralysis and even death; there are important blood vessels such as the vertebral artery around the atlantoaxial spine, once damaged, it can cause consequences of cerebellar infarction or death. (c) After lesion removal, the reconstruction of the spine is particularly difficult; at present, clinically used spinal fixation devices include posterior pedicle screw rods, cervical vertebra anterior plates and so on; however, these fixation devices are mainly designed for the lower cervical spine, and ordinary cervical vertebra titanium plates are not suitable for the fixation of the atlantoaxial spine; and the common titanium mesh is a cylindrical column with the same diameter, thus it cannot meet the reconstruction needs of the complicated anatomical shape of the atlantoaxial spine. Although domestic and overseas scholars have improved implants such as titanium meshes and have applied them to the reconstruction after atlantoaxial resection, deficiencies of application of the improved implants still exist, thus the improved implants can hardly meet the requirements of complicated surgeries; wherein the deficiencies could be fixation difficulties, poor shape matching, high failure rate of internal fixation after surgery, and low fusion rate after surgery.

SUMMARY

For solving the abovementioned problems, the present invention provides an artificial epistropheus support body which can be easily fastened, having good shape matching, low failure rate of internal fixation after surgery and high fusion rate after surgery. Hence, the artificial epistropheus support body can meet the requirements of complicated surgeries.

The technical solution provided by the present invention for solving the technical problems indicates as follows: an artificial epistropheus support body comprising a support, wherein the support comprises a crown part which can contact and support the facies articularis inferior of the atlas and a body part which can contact and support the third cervical vertebra; wherein a top surface of the crown part forms a top profiling surface that can closely fit with the facies articularis inferior of the atlas, and a bottom surface of the body part forms a bottom profiling surface that can closely fit with the facies articularis superior of the third cervical vertebra; the support has a cavity inside thereof, and a micro-hole grid stent is arranged in the cavity; the cavity forms a plurality of windows on the surface of the support; the bottom end of the body part is provided with a lower fixing lug, while the upper end of the crown part is provided with an upper fixing lug; both the lower fixing lug and the upper fixing lug are provided with fixing holes; the support can be fastened to the atlas through a screw passing through the fixing hole on the upper fixing lug, and the support can be fastened to the third cervical vertebra through a screw passing through the fixing hole on the lower fixing lug.

As a preferred embodiment of the present invention, the support has the cavity that penetrates from the top end surface to the bottom end surface, and the micro-hole grid stent is arranged around the inner wall of the cavity; wherein a through hole penetrating from the top end surface to the bottom end surface is configured within the micro-hole grid stent.

As a preferred embodiment of the present invention, the crown part, the body part, the micro-hole grid stent, the upper fixing lug and the lower fixing lug are manufactured by 3D printing in a way of unibody.

As a preferred embodiment of the present invention, the cavity forms windows on a front surface, a rear surface, a left surface, a right surface, a top surface and a bottom surface of the support.

As a preferred embodiment of the present invention, there are two upper fixing lugs, protruding upwards from the left and right flanks of a rear wall of the crown part, respectively; the lower fixing lug protrudes downwards from a rear wall of the body part, wherein two fixing holes in up and down staggered distribution are arranged on the lower fixing lug.

As a further preferred embodiment of the present invention, the upper fixing lug and the lower fixing lug are respectively provided with bowl-shaped grooves at apertures of the corresponding fixing holes, wherein the direction of a screw can be flexibly adjusted in each of the bowl-shaped grooves.

As a more preferred embodiment of the present invention, the upper fixing lug and the lower fixing lug are respectively provided with locking mechanisms capable of locking the screws on the side of the apertures of the corresponding fixing holes.

As a more preferred embodiment of the present invention, each of the locking mechanisms comprises a recess and a pressing cap;

wherein the recess is configured on one side of the aperture of each fixing hole;

wherein the pressing cap which is rotatably installed in the recess can partially cover the aperture of the fixing hole; wherein a groove for screwing is configured on the top end of the pressing cap, which is provided with a gap for assembling and disassembling the screw.

As a more preferred embodiment of the present invention, the artificial epistropheus support body further comprises an upper fixing lug drilling guide plate and a lower fixing lug drilling guide plate;

wherein the upper fixing lug drilling guide plate has an inner surface capable of fitting with the outer surface of the atlas; the outer surface of the upper fixing lug drilling guide plate is provided with two upper drilling pipes protruding outwards; the two upper drilling pipes pointing to the direction of the pedicle of the atlas are corresponding to the two fixing holes of the upper fixing lugs;

wherein the lower fixing lug drilling guide plate has an inner surface capable of fitting with the outer surface of the third cervical vertebra; the outer surface of the lower fixing lug drilling guide plate is provided with two lower drilling pipes protruding outwards; the two lower drilling pipes pointing to the direction of the pedicle of third cervical vertebra are corresponding to the two fixing holes of the lower fixing lug.

As a more preferred embodiment of the present invention, both the upper fixing lug drilling guide plate and the lower fixing lug drilling guide plate are manufactured by 3D printing in a way of unibody.

The beneficial effects of the present invention include: when the artificial epistropheus support body is applied for surgery, the reverse vertebral pedicle screw channel of the atlas and the reverse vertebral pedicle screw channel of the third cervical vertebra can be established on the outer surfaces of the atlas and the third cervical vertebra, respectively; the artificial epistropheus support body with appropriate type and size is selected and imbedded into the bone defect region; wherein the support is fastened to the reverse vertebral pedicle screw channel of the atlas through a screw passing through the fixing hole on the upper fixing lug, meanwhile, the support is fastened to the reverse vertebral pedicle screw channel of the third cervical vertebra through a screw passing through the fixing hole on the lower fixing lug. At this time, the artificial epistropheus support body forms a curved surface that gradually bulges upwards from the shoulder to the middle on the top surface of the crown part, thus the support can be in contact with and support the facies articularis inferior of the atlas via the curved surface, and be in contact with and support the facies articularis superior of the third cervical vertebra via the bottom surface of the body part, so the upper and lower ends of the support can excellently fit with the anatomical structure, completely simulating the structure and shape of the human epistropheus. Accordingly, the structure and shape of the artificial epistropheus support body is able to perfectly fill in defect sites caused by tumor resection and effectively exert the supporting function. The artificial epistropheus support body possesses good stability for supporting and reconstructing, it also can prevent a prosthesis from loosening and failing after surgery. Consequently, it is convenient to secure the artificial epistropheus support body with outstanding shape matching, so it provides low failure rate of internal fixation and high fusion rate after surgery, meeting the needs of complicated surgeries. Furthermore, the artificial epistropheus support body provided by the present invention is designed for simulating cancellous bones which are microporous, thus facilitating new bone ingrowth. The center of the prosthesis may be designed to be filled with autologous bone materials so as to increase the success rate of inducing osteogenesis.

BRIEF DESCRIPTION OF THE DRAWINGS

The present invention will be further described below with reference to the accompanying drawings.

DETAILED DESCRIPTION

Figure 1:
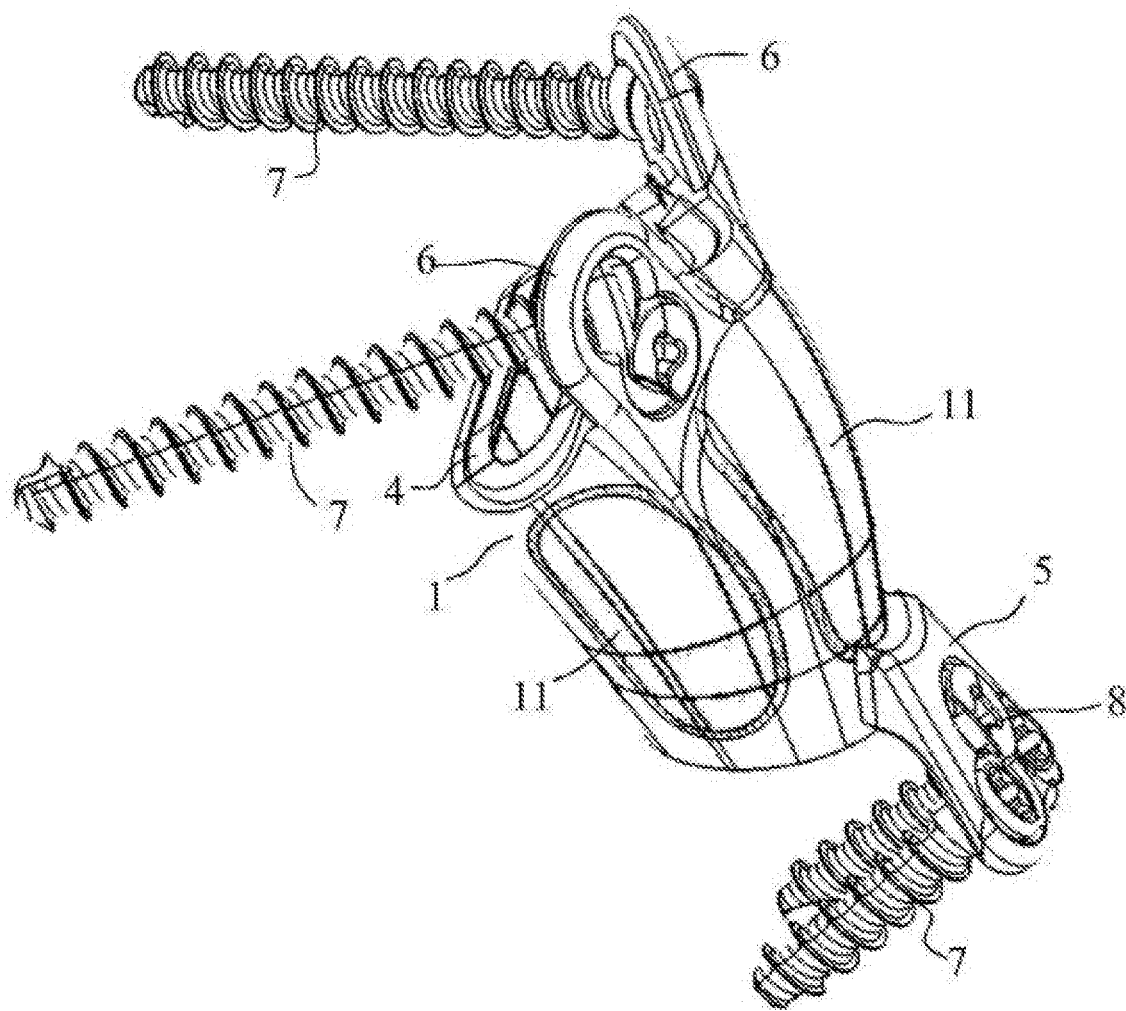
FIG. 1 is an axonometric view of a structure of an embodiment according to the present invention.
Figure 2:
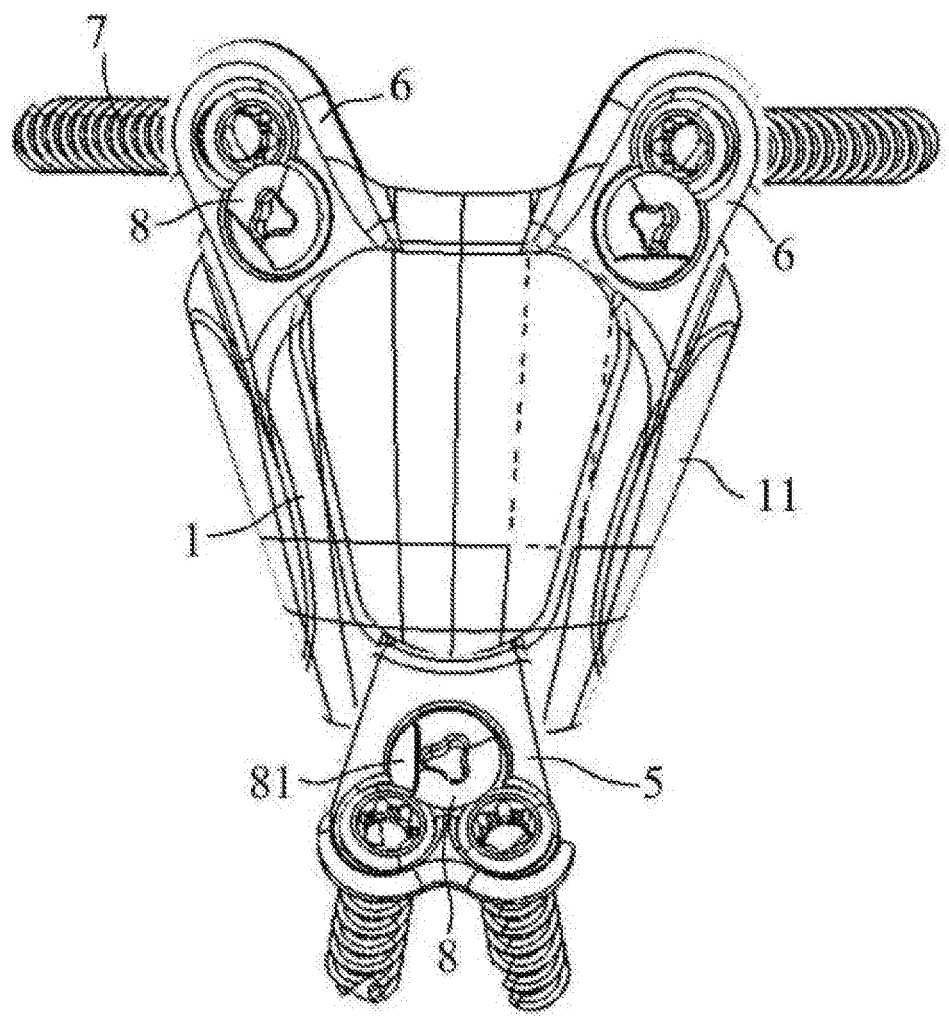
FIG. 2 is a front view of a structure of an embodiment according to the present invention.
Figure 3:
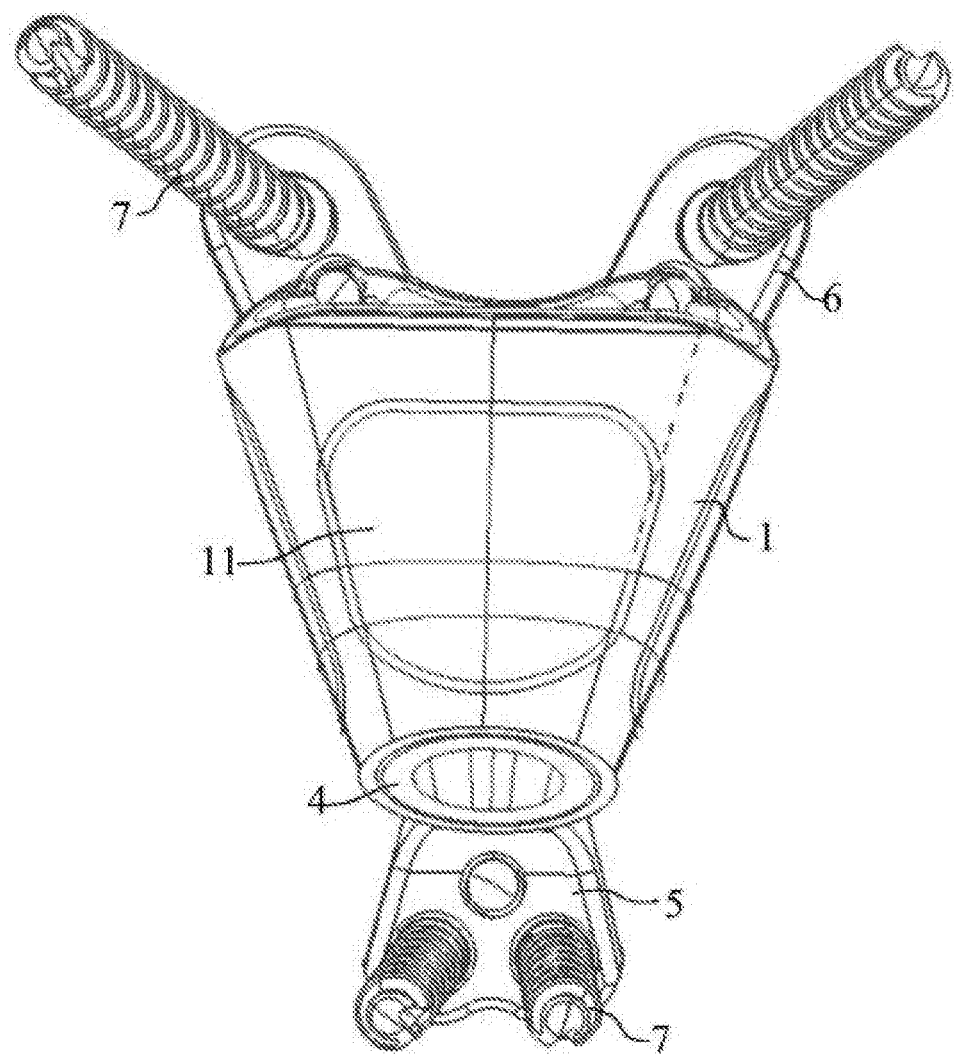
FIG. 3 is a rear view of a structure of an embodiment according to the present invention.
Figure 4:
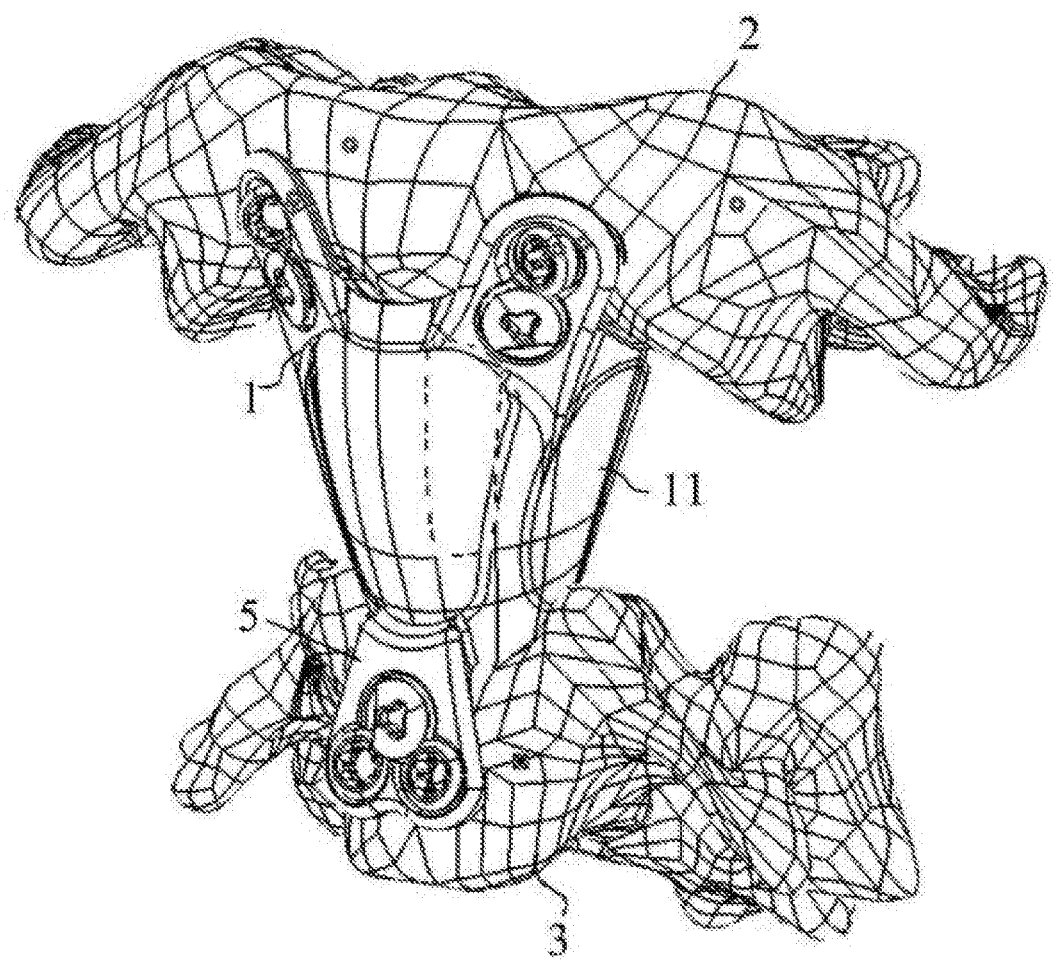
FIG. 4 is a structural schematic diagram of a state of use of an embodiment according to the present invention.

Referring to FIGS. 1-6, a specific structure of a preferred embodiment according to the present invention is shown therein. The following contents are intended to describe the structural features of elements of the present invention in details, when the description mentions directions (such as upward side, downward side, left, right, front and back), the structure shown in FIG. 2 is considered as the reference standard, but the actual directions where the present invention is applied are not limited to this.

Currently, commercial orthopeadic implants include commonly used vertebral pedicle screws, titanium rods, titanium meshes, artificial vertebrae and the like. These commercial orthopeadic implants are produced in accordance with unified specification, with mass production. Specifically, the screws and titanium meshes used in the neck, thorax, lumbar spine, etc. are identical in shape, the only difference among them is change in size, which could be enlarged and reduced based on different positions. This is applicable to a regular spine that is cylindrical in shape. However, with respect to the atlas, even if the cylindrical shape of an ordinary titanium mesh is changed in size, it will be difficult to meet the requirements of a reconstructive surgery. As everyone knows, the computer simulation technology can be used to simulate defect sites caused by epistropheus resection operation; if a conventional titanium mesh is implanted, the lower end of the titanium mesh could fit with the superior endplate of the third cervical vertebra, but the upper end of the titanium mesh could not anatomically fit with the lateral mass articular surface of the atlas, so that the support and reconstruction of which are unstable, thus inevitably leading to the looseness and failure of a prosthesis after surgery.

With the advent of the metal 3D printing technology, it is possible to design and customize complicated implants for spinal operation. The so-called 3D printing technology is a new type of industrial manufacturing technology which obtains a three-dimensional structure through a gradually forming process by accumulating layers of metal or non-metal powders. The advantage of the 3D printing technology is that: as long as a computer can design three-dimensional structures and parts, they can be converted into STL files, which would be imported into a 3D printer to complete rapid manufacturing. The 3D printing technology is a revolutionary invention of modern industry, it is not only widely used in the fields of industrial design and art design, but also has gradually entered the medical field in the past 10 years, for example, it is used in sclerous tissues surgeries, particularly it has played a more and more important role in assisting orthopedic surgery. For example, for some complicated orthopedic surgeries, we can obtain a skeleton model of a patient by 3D printing, used for designing and planning a surgical project; additionally, we can also design a specialized surgical guide plate to assist the surgery. The emergence of metal 3D manufacturing technology means that the currently widely used implant materials and internal fixation devices in orthopedics department can be individually designed and customized according to different patients and different surgical sites. This kind of a totally new concept will revolutionise the production and manufacture of implants for the orthopedic surgery and the development of surgical operations.

The present invention fully utilizes the advantages of medico-engineering cooperation, and designs a porous titanium alloy reconstruction prosthesis that perfectly matches the anatomical shape features of the epistropheus. The artificial epistropheus not only exhibits an ideal supporting function, but also integrates the integrated neck 1 and neck 3 steel plate-screws fixing system. The customized guide apparatus is used to guide screws for atlas, and to implement a strong and reliable anterior fixation of the reverse vertebral pedicle screw of the neck 3 so as to meet the needs of a surgery, in order to obtain the optimal mechanical property.

Specifically, as shown in FIGS. 1-4, the present invention provides an artificial epistropheus support body comprising a support 1, wherein the support 1 comprises a crown part which can contact and support the facies articularis inferior of the atlas 2 and a body part which can contact and support the third cervical vertebra 3; wherein a top surface of the crown part forms a top profiling surface that can closely fit with the facies articularis inferior of the atlas 2, and a bottom surface of the body part forms a bottom profiling surface that can closely fit with the facies articularis superior of the third cervical vertebra 3; the support 1 has a cavity inside thereof, and a micro-hole grid stent 4 is arranged in the cavity; the cavity forms a plurality of windows 11 on a front surface, a rear surface, a left surface, a right surface, a top surface and a bottom surface of the support 1. The windows 11 and the micro-hole grid stent 4 provide support and space for bone ingrowth of the contact surface. Furthermore, the bottom end of the body part is provided with a lower fixing lug 5, the upper end of the crown part is provided with an upper fixing lug 6; both the lower fixing lug 5 and the upper fixing lug 6 are provided with fixing holes; the support 1 can be fastened to the atlas 2 through a screw 7 passing through the fixing hole on the upper fixing lug 6, and the support 1 can be fastened to the third cervical vertebra 3 through a screw 7 passing through the fixing hole on the lower fixing lug 5.

Specifically, the support 1 has the cavity that penetrates from the top end surface to the bottom end surface, and the micro-hole grid stent 4 is arranged around the inner wall of the cavity; wherein a through hole penetrating from the top end surface to the bottom end surface is configured within the micro-hole grid stent 4. All of the crown part, the body part, the micro-hole grid stent 4, the upper fixing lug 6 and the lower fixing lug 5 are manufactured by 3D printing in a way of unibody. Moreover, the present invention may utilize computer three-dimensional reconstruction and features extraction technology to design a personalized simulated cervical vertebra implant, which completely meets the needs of individualized cervical vertebra surgery. Meanwhile, the rapid production of prostheses using metal 3D printing manufacturing technology is an additive manufacturing technology, which overcomes the deficiencies of traditional subtractive manufacturing and processing technologies.

Preferably, there are two upper fixing lugs 6, protruding upwards from the left and right flanks of a rear wall of the crown part, respectively; the lower fixing lug 5 protrudes downwards from a rear wall of the body part, wherein two fixing holes in up and down staggered distribution are arranged on the lower fixing lug 5. It is noted that the two fixing holes in up and down staggered distribution can make the screws in the two fixing holes do not interfere with each other. Additionally, the upper fixing lugs 6 and the lower fixing lug 5 are respectively provided with bowl-shaped grooves at apertures of the corresponding fixing holes, wherein the direction of a screw can be flexibly adjusted in each of the bowl-shaped grooves. The upper fixing lugs 6 and the lower fixing lug 5 are respectively provided with locking mechanisms capable of locking the screws on the side of the apertures of the corresponding fixing holes; wherein each of the locking mechanisms comprises a recess and a pressing cap 8; wherein the recess is configured on one side of the aperture of each fixing hole; wherein the pressing cap 8 which is rotatably installed in the recess can partially cover the aperture of the fixing hole. A groove for screwing is configured on the top end of the pressing cap 8, wherein the groove for screwing is formed in a polygonal shape or a cross shape. The pressing cap 8 is provided with a gap 81 for assembling and disassembling the screw. When the screw 7 is about to be inserted, the pressing cap 8 is rotated via the groove for screwing so that the gap 81 keeps away from the aperture of the fixing hole; after the screw 7 is fastened, the pressing cap 8 is rotated again, so that the pressing cap 8 partially covers and presses the screw 7 tightly, to avoid loosening.

Figure 5:
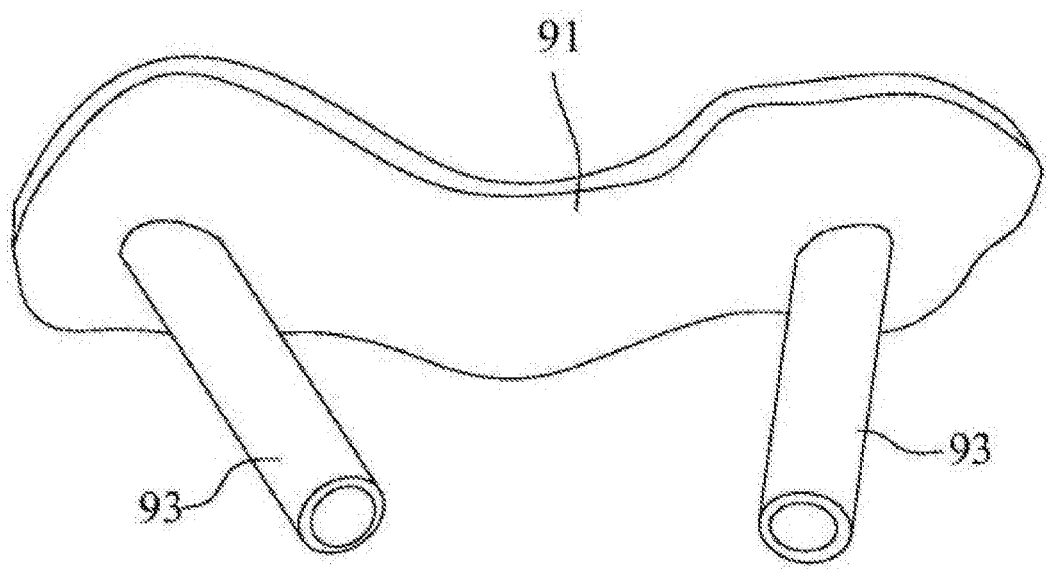
FIG. 5 is a structural schematic diagram of an upper fixing lug drilling guide plate according to the present invention.
Figure 6:
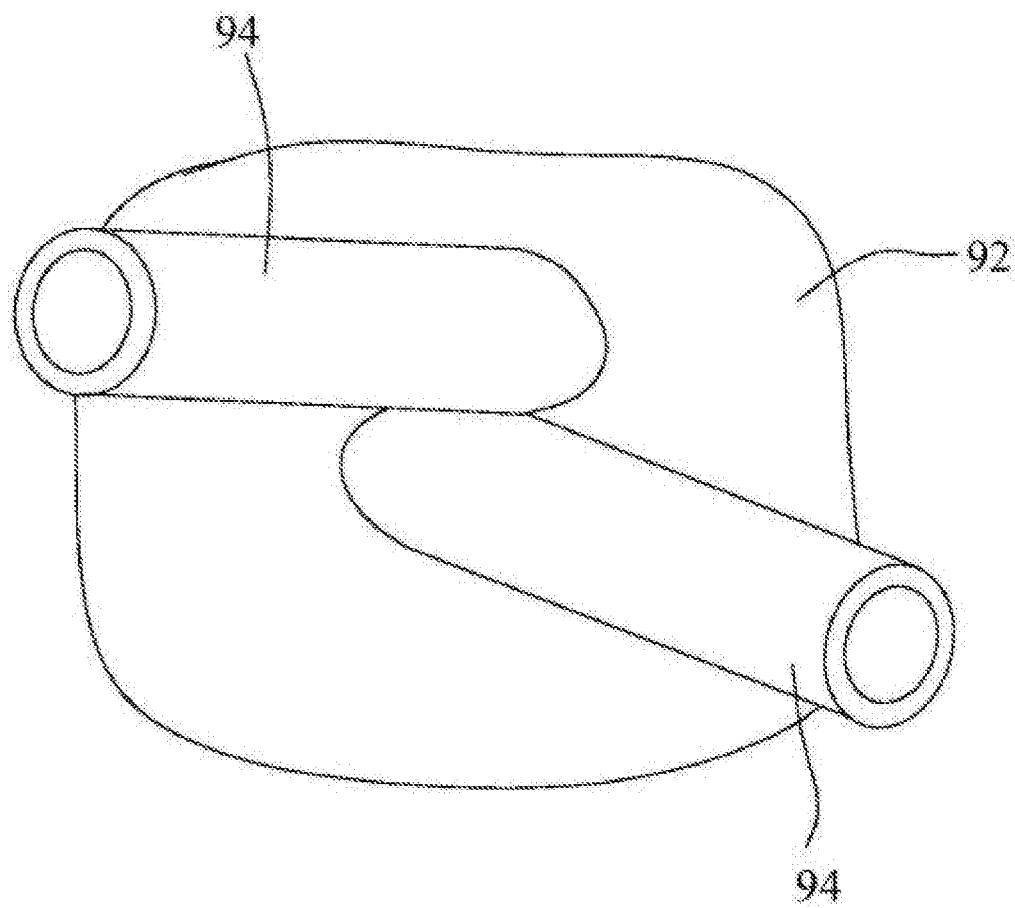
FIG. 6 is a structural schematic diagram of a lower fixing lug drilling guide plate according to the present invention.

As shown in FIGS. 5 and 6, the artificial epistropheus support body further comprises an upper fixing lug drilling guide plate 91 and a lower fixing lug drilling guide plate 92; wherein both the upper fixing lug drilling guide plate 91 and the lower fixing lug drilling guide plate 92 are manufactured by 3D printing in a way of unibody. Additionally, the upper fixing lug drilling guide plate 91 has an inner surface capable of fitting with the outer surface of the atlas; the outer surface of the upper fixing lug drilling guide plate 91 is provided with two upper drilling pipes 93 protruding outwards; the two upper drilling pipes 93 pointing to the direction of the pedicle of the atlas are corresponding to the two fixing holes of the upper fixing lugs 6; wherein the screw that guides one of the upper fixing lugs 6 can enter into the vertebral pedicle of the atlas through the lateral mass of the atlas. The lower fixing lug drilling guide plate 92 has an inner surface capable of fitting with the outer surface of the third cervical vertebra 3; the outer surface of the lower fixing lug drilling guide plate 92 is provided with two lower drilling pipes 94 protruding outwards; the two lower drilling pipes 94 pointing to the direction of the pedicle of third cervical vertebra 3 are corresponding to the two fixing holes of the lower fixing lug 5. The screw that guides the lower fixing lug 5 can enter into the vertebral pedicle through the third cervical vertebra 3. Since important nerves and blood vessels exist around the atlas 2 and the epistropheus, the screws 7 must be accurately implanted into the atlas and the pedicle of third cervical vertebra 3, in order to effectively prevent nerves and blood vessels being damaged. The technical solution uses reverse engineering technology to design the upper fixing lug drilling guide plate 91 and the lower fixing lug drilling guide plate 92, with the assistance of computer aided design, and to guide the establishment of a screw channel and safe implantation of the screw, so as to ensure that the screw is accurately and safely implanted in the vertebra in accordance with the preoperative design intent, without damaging nerves and blood vessels.

A surgery with the artificial epistropheus support body is exemplified as follows:

Step 1: A patient is placed in a supine position, propping shoulders up, tilting the head back, connected to skull traction, so as to ensure that the atlas undergoes a surgery in a reset state.

Step 2: Prior to the surgery, the mouth was washed repeatedly with chlorhexidine, iodophor, and saline, and the sterilization and drape was completed; make an incision at the middle of the posterior pharyngeal wall, and cut the mucous membrane and the submucous muscular layer, then use an electrotome to peel off the anterior cervical muscles in order to expose the anterior arch of the atlas, lateral mass of the atlas, the vertebral body in the front of the epistropheus and lateral mass joints on both sides.

Step 3: the electrotome is further used to cut released bilateral lateral joint capsules of the atlantoaxial spine, reserve a quarter of the external; pay attention to the vertebral artery and avoid injury.

Step 4: Peel off the soft tissues in front of the first to third cervical vertebra so as to fully reveal the anterior structures of first to third cervical vertebra.

Step 5: The upper fixing lug drilling guide plate of the atlas is fastened to the surface of the atlas, fitting closely; then drill along the direction of one upper drilling pipe, in order to establish a reverse vertebral pedicle screw channel of the atlas.

Step 6: Implement the same process as described above, the lower fixing lug drilling guide plate of the third cervical vertebra is fastened to the surface of the third cervical vertebra, fitting closely; then drill along the direction of one lower drilling pipe, in order to establish a reverse vertebral pedicle screw channel of the third cervical vertebra.

Step 7: The second cervical vertebra is completely resected with a tool such as a high-speed burr, with careful hemostasis.

Step 8: The support is implanted into the defect region after the excision of the second cervical vertebra, and a screw with suitable length is selected and screwed into a pre-prepared screw channel for fixation. The above descriptions are only the preferred embodiments of the invention, not thus limiting the embodiments and scope of the invention. Those skilled in the art should be able to realize that the schemes obtained from the contents of the specification and drawings of the invention are within the scope of the invention.

What is claimed is:

1. An artificial epistropheus support body comprising a support, wherein the support comprises a crown part contacting and supporting facies articularis inferior of an atlas and a body part contacting and supporting a third cervical vertebra;
   a top surface of the crown part forms a top profiling surface closely fitting with the facies articularis inferior of the atlas, and a bottom surface of the body part forms a bottom profiling surface closely fitting with the facies articularis superior of the third cervical vertebra;
   the support has a cavity inside thereof;
   wherein the cavity penetrates from a top end surface of the support to a bottom end surface of the support, wherein the cavity forms a plurality of windows on a front surface, a rear surface, a left surface, a right surface, a top surface and a bottom surface of the support and a micro-hole grid stent is arranged around an inner wall of the cavity; wherein a through hole penetrates within the micro-hole grid stent;
   a bottom end of the body part is provided with a lower fixing lug, while an upper end of the crown part is provided with an upper fixing lug; both the lower fixing lug and the upper fixing lug are provided with fixing holes; the support can be fastened to the atlas through a first screw passing through the fixing hole on the upper fixing lug, and the support can be fastened to the third cervical vertebra through a second screw passing through the fixing hole on the lower fixing lug.

2. The artificial epistropheus support body according to claim 1, wherein the crown part, the body part, the micro-hole grid stent, the upper fixing lug and the lower fixing lug are manufactured by 3D printing in a way of unibody.

3. The artificial epistropheus support body according to claim 1, wherein an amount of the upper fixing lugs is two, the two upper fixing lugs protrude upwards from left and right flanks of a rear wall of the crown part, respectively; the lower fixing lug protrudes downwards from a rear wall of the body part, an amount of the fixing holes is two, and the two fixing holes in up and down staggered distribution are arranged on the lower fixing lug.

4. The artificial epistropheus support body according to claim 3, wherein the upper fixing lug and the lower fixing lug are respectively provided with bowl-shaped grooves at apertures of corresponding fixing holes, wherein a direction of the screws can be flexibly adjusted in each of the bowl-shaped grooves.

5. The artificial epistropheus support body according to claim 4, wherein the upper fixing lug and the lower fixing lug are respectively provided with locking mechanisms that lock the screws on a side of the apertures of the corresponding fixing holes.

6. The artificial epistropheus support body according to claim 5, wherein each of the locking mechanisms comprises a recess and a pressing cap;
   the recess is configured on one side of the aperture of each of the fixing holes;
   the pressing cap rotatably installed in the recess partially covers the aperture of the fixing hole; a groove for screwing is configured on a top end of the pressing cap, which is provided with a gap for assembling and disassembling the screw.

7. The artificial epistropheus support body according to claim 3, wherein the artificial epistropheus support body further comprises an upper fixing lug drilling guide plate and a lower fixing lug drilling guide plate;
   the upper fixing lug drilling guide plate has an inner surface capable of fitting with an outer surface of the atlas; an outer surface of the upper fixing lug drilling guide plate is provided with two upper drilling pipes protruding outwards; the two upper drilling pipes pointing to a direction of a pedicle of the atlas are corresponding to the two fixing holes of the upper fixing lugs;
   the lower fixing lug drilling guide plate has an inner surface capable of fitting with an outer surface of the third cervical vertebra; an outer surface of the lower fixing lug drilling guide plate is provided with two lower drilling pipes protruding outwards; the two lower drilling pipes pointing to a direction of a pedicle of the third cervical vertebra are corresponding to the two fixing holes of the lower fixing lug.

8. The artificial epistropheus support body according to claim 7, wherein both the upper fixing lug drilling guide plate and the lower fixing lug drilling guide plate are manufactured by 3D printing in a way of unibody.

9. The artificial epistropheus support body according to claim 3, wherein the crown part, the body part, the microhole grid stent, the upper fixing lug and the lower fixing lug are manufactured by 3D printing in a way of unibody.

10. The artificial epistropheus support body according to claim 2, wherein an amount of upper fixing lugs is two, the two upper fixing lugs protrude upwards from left and right flanks of a rear wall of the crown part, respectively; the lower fixing lug protrudes downwards from a rear wall of the body part, an amount of the fixing holes is two, and the two fixing holes in up and down staggered distribution are arranged on the lower fixing lug.

11. The artificial epistropheus support body according to claim 10, wherein the upper fixing lug and the lower fixing lug are respectively provided with bowl-shaped grooves at apertures of corresponding fixing holes, wherein a direction of the screws can be flexibly adjusted in each of the bowl-shaped grooves.

12. The artificial epistropheus support body according to claim 11, wherein the upper fixing lug and the lower fixing lug are respectively provided with locking mechanisms that lock the screws on a side of the apertures of the corresponding fixing holes.

13. The artificial epistropheus support body according to claim 12, wherein each of the locking mechanisms comprises a recess and a pressing cap;
the recess is configured on the side of the aperture of each of the fixing holes;
the pressing cap rotatably installed in the recess partially covers the aperture of the fixing hole; a groove for screwing is configured on a top end of the pressing cap, which is provided with a gap for assembling and disassembling the screw.

14. The artificial epistropheus support body according to claim 10, wherein the artificial epistropheus support body further comprises an upper fixing lug drilling guide plate and a lower fixing lug drilling guide plate;
the upper fixing lug drilling guide plate has an inner surface capable of fitting with an outer surface of the atlas; an outer surface of the upper fixing lug drilling guide plate is provided with two upper drilling pipes protruding outwards; the two upper drilling pipes pointing to a direction of a pedicle of the atlas are corresponding to the two fixing holes of the upper fixing lugs;
the lower fixing lug drilling guide plate has an inner surface capable of fitting with an outer surface of the third cervical vertebra; an outer surface of the lower fixing lug drilling guide plate is provided with two lower drilling pipes protruding outwards; the two lower drilling pipes pointing to a direction of a pedicle of the third cervical vertebra are corresponding to the two fixing holes of the lower fixing lug.

15. The artificial epistropheus support body according to claim 14, wherein both the upper fixing lug drilling guide plate and the lower fixing lug drilling guide plate are manufactured by 3D printing in a way of unibody.

16. The artificial epistropheus support body according to claim 1, wherein the artificial epistropheus support body is made from porous titanium alloy.

\* \* \* \* \*